(12) United States Patent
Moller et al.

(10) Patent No.: US 8,357,120 B2
(45) Date of Patent: *Jan. 22, 2013

(54) INJECTION DEVICE WITH TORSION SPRING AND ROTATABLE DISPLAY

(75) Inventors: Claus Schmidt Moller, Fredensborg (DK); Tom Hede Markussen, Bagsværd (DK); Christian Peter Enggaard, Vejby (DK)

(73) Assignee: Novo Nordisk A/S, Bagsvaerd (DK)

(*) Notice: Subject to any disclaimer, the term of this patent is extended or adjusted under 35 U.S.C. 154(b) by 12 days.

This patent is subject to a terminal disclaimer.

(21) Appl. No.: 11/665,571

(22) PCT Filed: Oct. 20, 2005

(86) PCT No.: PCT/EP2005/011287
§ 371 (c)(1), (2), (4) Date: Dec. 5, 2007

(87) PCT Pub. No.: WO2006/045528
PCT Pub. Date: May 4, 2006

(65) Prior Publication Data
US 2009/0054839 A1    Feb. 26, 2009

Related U.S. Application Data

(60) Provisional application No. 60/626,271, filed on Nov. 9, 2004.

(30) Foreign Application Priority Data

Oct. 21, 2004  (EP) ..................................... 04077899

(51) Int. Cl.
*A61M 5/20* (2006.01)

(52) U.S. Cl. ........................................ 604/135; 604/207
(58) Field of Classification Search .................. 604/135, 604/131, 134, 181, 207–211, 224, 218
See application file for complete search history.

(56) References Cited

U.S. PATENT DOCUMENTS

| 4,393,723 A | 7/1983 | Brand |
| 4,865,591 A | 9/1989 | Sams |

(Continued)

FOREIGN PATENT DOCUMENTS

| AU | 2003232576 | 1/2004 |
| CA | 2359375 | 7/2000 |

(Continued)

OTHER PUBLICATIONS

Machine Translation of DE20317377 as Made by espacenet.

(Continued)

*Primary Examiner* — Nicholas D Lucchesi
*Assistant Examiner* — Laura A Bouchelle
(74) *Attorney, Agent, or Firm* — Marc A. Began (57) ABSTRACT

The present invention relates to an injection device comprising a torsion spring operatively connected to a dose setting member being adapted to set a dose to be ejected from the injection device. A rotatably mounted display member adapted to display the dose to be ejected in accordance with a setting of the dose setting member is also provided. The rotatably mounted display member is adapted to be rotated over an angle corresponding to at least one revolution of the display member. The display member may be implemented as a dose indicator barrel having numerals arranged along a helical path on an outer surface thereof, or alternatively, as a counting device having two or more display wheels having numerals arranged on an outer surface thereof.

30 Claims, 5 Drawing Sheets

U.S. PATENT DOCUMENTS

| | | | |
|---|---|---|---|
| 5,104,380 A | 4/1992 | Holman et al. | |
| 5,104,388 A | 4/1992 | Quackenbush | |
| 5,114,406 A | 5/1992 | Gabriel et al. | |
| 5,226,896 A | 7/1993 | Harris | |
| 5,292,976 A | 3/1994 | Dessau et al. | |
| 5,295,976 A | 3/1994 | Harris | |
| 5,308,340 A | 5/1994 | Harris | |
| 5,320,609 A | 6/1994 | Haber et al. | |
| 5,383,856 A | 1/1995 | Bersin | |
| 5,383,865 A | 1/1995 | Michel | |
| 5,480,387 A | 1/1996 | Gabriel et al. | |
| 5,591,136 A | 1/1997 | Gabriel | |
| 5,626,566 A | 5/1997 | Petersen et al. | |
| 5,725,508 A | 3/1998 | Chanoch et al. | |
| 5,820,602 A | 10/1998 | Kovelman et al. | |
| 5,827,232 A | 10/1998 | Chanoch et al. | |
| 5,921,966 A | 7/1999 | Bendek et al. | |
| 6,004,297 A | 12/1999 | Steenfeldt-Jensen et al. | |
| 6,048,336 A | 4/2000 | Gabriel | |
| 6,419,661 B1 * | 7/2002 | Kuhr et al. | 604/207 |
| 6,666,849 B1 | 12/2003 | Marshall et al. | |
| 6,699,224 B2 | 3/2004 | Kirchhofer et al. | |
| 6,899,699 B2 | 5/2005 | Enggaard | |
| 7,500,966 B2 | 3/2009 | Hommann | |
| 2001/0053893 A1 * | 12/2001 | Larsen | 604/207 |
| 2002/0016571 A1 | 2/2002 | Kirchhofer et al. | |
| 2002/0165500 A1 | 11/2002 | Bechtold et al. | |
| 2002/0173752 A1 | 11/2002 | Polzin | |
| 2005/0197625 A1 * | 9/2005 | Haueter et al. | 604/131 |
| 2006/0258988 A1 | 11/2006 | Keitel et al. | |

FOREIGN PATENT DOCUMENTS

| | | |
|---|---|---|
| DE | 3638984 | 5/1988 |
| DE | 4223958 | 1/1993 |
| DE | 29513214 | 2/1997 |
| DE | 19723647 | 12/1998 |
| DE | 19838760 | 4/2000 |
| DE | 29907880 | 9/2000 |
| DE | 10103287 | 8/2001 |
| DE | 10229122 | 2/2004 |
| DE | 20317377 | 3/2005 |
| EP | 327910 | 8/1989 |
| EP | 338806 | 10/1989 |
| EP | 554996 | 8/1993 |
| EP | 1000631 | 10/1997 |
| EP | 608343 | 12/1997 |
| EP | 897728 | 2/1999 |
| EP | 937472 | 8/1999 |
| EP | 937476 | 8/1999 |
| EP | 1003581 | 8/1999 |
| EP | 1351732 | 6/2005 |
| EP | 1610848 | 4/2006 |
| EP | 1819382 | 10/2009 |
| GB | 0007071.4 | 3/2000 |
| JP | 4-224764 | 8/1992 |
| JP | 7-500039 | 3/1994 |
| JP | 2002501790 A | 1/2002 |
| JP | 2004503303 | 2/2004 |
| JP | 2004516895 | 6/2004 |
| JP | 2007/509662 A | 4/2007 |
| JP | 2007509662 | 4/2007 |
| RU | 2091087 | 9/1997 |
| RU | 2212254 | 9/2003 |
| WO | WO9307922 | 4/1993 |
| WO | WO96/32973 | 10/1996 |
| WO | WO9938554 | 8/1999 |
| WO | WO 01/10484 | 2/2001 |
| WO | WO 01/19434 | 3/2001 |
| WO | WO 01/30425 | 5/2001 |
| WO | WO 01/72361 | 10/2001 |
| WO | WO 01/95959 | 12/2001 |
| WO | WO 02/053214 | 7/2002 |
| WO | WO02053214 | 7/2002 |
| WO | WO 02/092153 | 11/2002 |
| WO | WO 2004/002556 | 1/2004 |
| WO | WO2004/024218 | 3/2004 |
| WO | WO2004/028598 | 4/2004 |
| WO | WO2004/078240 | 9/2004 |
| WO | WO 2005/046770 | 5/2005 |
| WO | WO2006/045528 | 5/2006 |

OTHER PUBLICATIONS

English Abstract of JP7-500039.
English Abstract of RU 2091087.
English Abstract of RU 2212254.
Non-Final Office Action in U.S. Appl. No. 10/970,868, filed Oct. 22, 2004; First Named Inventor: Christian Enggaard, Dated Apr. 12, 2007.
Final Office Action in U.S. Appl. No. 10/970,868, filed Oct. 22, 2004; First Named Inventor: Christian Enggaard, Dated Dec. 31, 2007.
Non-Final Office Action in U.S. Appl. No. 10/970,868, filed Oct. 22, 2004; First Named Inventor: Christian Enggaard, Dated Jul. 31, 2008.
Final Office Action in U.S. Appl. No. 10/970,868, filed Oct. 22, 2004; First Named Inventor: Christian Enggaard, Dated Mar. 2, 2009.
Non-Final Office Action in U.S. Appl. No. 10/970,868, filed Oct. 22, 2004; First Named Inventor: Christian Enggaard, Dated Jan. 19, 2010.
Owen Mumford Product Range Making a World of Difference.
English Abstract of DE19838760.
Final Office Action Mailed Jun. 30, 2010 in U.S. Appl. No. 10/970,868, filed Oct. 22, 2004; First Named Inventor: Christian Enggaard.
Communication of a Notice of Opposition Dated Jul. 13, 2010 by Owen Mumford (EP 1 819 382).
Communication of a Notice of Opposition Dated Jul. 14, 2010 by Genentech (EP 1 819 382).
Communication of a Notice of Opposition Dated Jul. 14, 2010 by Copernicus (EP 1 819 382).
Communication of a Notice of Opposition Dated Jul. 16, 2010 by Ypsomed (EP 1 819 382).
Communication of a Notice of Opposition Dated Jul. 20, 2010 by Stockeler (EP 1 819 382).
Communication of a Notice of Opposition Dated Jul. 13, 2010 by Ferring (EP 1 819 382).
Communication of Notice of Opposition Dated Mar. 1, 2006 by Owen Mumford (EP 1 351 732).
Communication of Notice of Opposition Dated Mar. 6, 2006 by Genentech (EP 1 351 732).
Communication of Notice of Opposition Dated Mar. 7, 2006 by Techpharma (EP 1 351 732).
Validity Opinion by the UK PTO.

* cited by examiner

INJECTION DEVICE WITH TORSION SPRING AND ROTATABLE DISPLAY

CROSS-REFERENCE TO RELATED APPLICATIONS

This application is a 35 U.S.C. §371 national stage application of International Patent Application PCT/EP2005/011287 (published as WO 2006/045528), filed Oct. 20, 2005, which claimed priority of European Patent Application 04077899.5, filed Oct. 21, 2004; this application further claims priority under 35 U.S.C. §119 of U.S. Provisional Application 60/626,271, filed Nov. 9, 2004.

FIELD OF THE INVENTION

The present invention relates to an injection device, such as a wind-up pen, wherein numerals indicating the dose to be ejected from the injection device are displayed over an angle of rotation exceeding one revolution. In particular, the numerals indicating the dose to be ejected are arranged along a helical path, or alternatively, numerals indicating the dose to be ejected are displayed on a counting device. The present invention ensures that an increased accuracy in dose setting may be obtained.

BACKGROUND OF THE INVENTION

Various types of automatic injection devices have been described in the literature. A majority of these automatic injection devices apply dose indicator barrels, dose indicator wheels or the like which, during dose setting, are only allowed to rotate less than one single revolution. The fact that the dose indicator barrel is only allowed to rotate less than one revolution during dose setting puts a limit to the obtainable angular resolution. This limited angular resolution also limits the accuracy of the dose setting procedure.

In prior art injection devices the dose setting scale arranged on the outer surface of the barrels or wheels contains only up to 42 scale units with an incremental of 2. Thus, the accuracy when setting a dose is limited by this rather rough incremental.

Examples of "one revolution" barrels or wheel may for example be found in U.S. Pat. No. 5,725,508, EP 0 338 806 or U.S. Pat. No. 5,104,380.

WO 02/053214 discloses an automatic injection device having a dose indicator barrel capable of rotating more than one revolution. However, the injection device according to WO 02/053214 applies a linear spring to move a piston rod in the distal direction of the injection device. Evidently, an injection device applying a linear spring has a built-in axial displacement due to compressions and extensions of the linear spring along the axial direction of the injection device. This linear movement may easily be utilized to provide axial movements of the dose indicator barrel. However, it is a disadvantage that linear springs are highly non-linear in terms of force vs. compression. In addition, a linear spring exhibits relative high mechanical looses. Thus, due to the problems relating to the non-linear properties and relatively high looses there is a need for injection devices having linear and more efficient injection assisting systems.

The above-mentioned problems may be solved by applying a torsion spring instead of the linear spring. An injection device applying a torsion spring is conceptually different from linear spring-based devices in that torsion-based systems do not have a built-in axial movement of the spring assisting the user in injecting a dose of medicament from the injection device. The advantages of torsion-based injection devices are many, the greatest of these probably being that torsion springs respond in a linear manner over a large working range.

Thus, there is a need for a torsion spring-based injection device providing an improved and more user friendly dose setting procedure. It is an object of the present invention to provide such torsion spring-based injection device having an expanded dose scale with a high resolution.

SUMMARY OF THE INVENTION

The above-mentioned object is complied with by providing, in a first aspect, an injection device comprising
 a torsion spring operatively connected to a dose setting member, the dose setting member being adapted to set a dose to be ejected from the injection device, and
 a rotatably mounted display member adapted to display the dose to be ejected from the injection device in accordance with a setting of the dose setting member, the rotatably mounted display member being rotatable over an angle corresponding to at least one revolution of the display member.

The display member may be adapted to be moved between two end positions. These two end positions may define or set an axial operation range of the display member. The axial operation range of the display member may be associated with a substantially linear working range of the torsion spring. The working range of the torsion spring utilized to move the display member between the two end positions may constitute only a fraction of the available working range provided by the torsion spring. Thus, by applying a torsion spring only a small and linear working range of the available working range is utilized.

The display member may comprise a dose indicator barrel having numerals arranged along a helical path on an outer surface thereof.

According to a first embodiment of the present invention, the injection device may further comprise
 a housing,
 a piston rod having a threaded outer surface with a drive track arranged in a longitudinal direction of the outer surface of the piston rod,
wherein the dose setting member is rotatably mounted and defines a passage for the piston rod, the dose setting member further having a guiding track arranged on an inner surface thereof,
 a rotatable drive member being adapted to at least partly engage with at least part of the drive track of the piston rod so as to drive the piston rod,
wherein the dose indicator barrel has a part engaging at least part of the guiding track of the dose setting member, the dose setting member and the dose indicator barrel being movable in relation to each other, the dose indicator barrel further having a threaded outer surface cooperating with a threaded inner portion of the housing whereby the close indicator barrel undergoes a combined translational and rotational movement in relation to the housing upon rotation of the dose setting member, and
wherein the injection device has a threaded portion cooperating with the threaded outer surface of the piston rod so that rotation of the piston rod relative to the housing results in a longitudinal movement of the piston rod.

It is to be understood that the drive track dose not necessarily extend over the full length of the piston rod. For example, the drive track may in some cases only extend over a part of the full length of the piston rod. Also, the drive track arranged in the piston rod may be an indentation or groove in the longitudinal direction of the piston rod. Alternatively, it may also be a planar surface or two opposing planar surfaces.

Similarly, it is to be understood that other arrangements in terms of the positioning of the threaded portion of for example the dose indicator barrel may be arranged differently.

According to a second embodiment of the present invention, the injection device further comprises a housing,
a piston rod having a threaded outer surface with a track arranged in a longitudinal direction of the outer surface of the piston rod,
wherein the dose setting member is rotatably mounted and defines a passage for the piston rod, the dose setting member further having a guiding track arranged on an inner surface thereof,
a rotatable drive member having a threaded portion cooperating with at least part of the threaded outer surface of the piston rod,
wherein the dose indicator barrel has a part engaging at least part of the guiding track of the dose setting member, the dose setting member and the dose indicator barrel being movable in relation to each other, the dose indicator barrel further having a threaded outer surface cooperating with a threaded inner portion of the housing whereby the dose indicator barrel undergoes a combined translational and rotational movement in relation to the housing upon rotation of the dose setting member, and
wherein the injection device has a portion at least partly engaging the track of piston rod so that rotation of the drive member relative to the housing results in a longitudinal movement of the piston rod.

The drive member may be adapted to be connected to the dose setting member via a ratchet. This ratchet allows the dose setting member to be rotated in both directions so that a given dose may be either increased or reduced. Due to the force provided by the torsion spring onto the ratchet, the dose setting member will remain in any position—i.e. dose value—to which it has been brought.

The dose setting member may be adapted to be separated from the driving member. This separation may be achieved in several ways. In one way the separation may be obtained by a retraction of the dose setting member in the axial direction of the injection device. The retraction of the dose setting member must be over a distance sufficient to detach the dose setting member or the drive member from the teeth of the ratchet. Other separation mechanisms, such as pushing the dose setting member or twisting the dose setting member are also applicable.

The torsion spring may be arranged between the housing and the dose setting member in such a way that when the dose setting member is rotated around the piston rod, the torsion spring is strained. The torsion spring may be a helical spring which extends coaxially with the piston rod, and which interconnects the housing and the dose setting member in such a way that rotation of the dose setting member, in order to set the dose, strains the torsion spring.

The injection device may further comprise a locking member adapted to fixate the piston rod in such a way that no relative rotation of the piston rod and the housing is possible when the locking member is in its locking position. This fixation may be provided by a direct engagement of the locking member into the track of the piston rod, or via the drive member. The injection device may further comprise a release button adapted to release the locking member from its locking position. Preferably, the release button is positioned in the distal half of the length of the injection device.

The injection device may further comprise a first stopping member for defining an outer position of the dose indicator barrel. This outer position of the dose indicator barrel may correspond to a maximum obtainable dose. Another outer position of the dose indicator barrel, given by a second stopping member, may define a stop for providing further doses. The stopping members may form integral parts of the inner surface of the housing.

In a third embodiment, the display member may comprise a counting device having two or more display wheels having numerals arranged on an outer surface thereof. In this second embodiment the counting device may have a first and a second wheel. When the dose setting member is rotated, the first wheel is rotated via an optional gear mechanism, such as a planet gear. This first wheel may contain numerals with an incremental of one. The total scale on this wheel may be from 0 to 9. The second wheel next to the first wheel also contains numerals with an incremental of 1. However, this second wheel "counts" the number of revolutions of the first wheel, or alternatively, it "counts" the tens of the first wheel with an incremental of one.

BRIEF DESCRIPTION OF THE DRAWINGS

The present invention will now be described in further details with reference to the accompanying figures, wherein.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE INVENTION

In its most general aspect the present invention relates to an injection device comprising a torsion spring in combination with a rotatable dose indicator mechanism capable of being rotated at least one revolution—i.e. over an angle larger than 360 degrees. For example, the dose indicator mechanism may be implemented as a barrel (see FIGS. 1-4) or as interconnected wheels (see FIG. 5), the latter being operated as a counting device. In order to increase the angular resolution compared to known dose indicator mechanisms the dose indicator mechanism of the present invention is rotatable over an angle of rotation corresponding to at least one revolution. The fact that the dose to be ejected is displayed over at least one revolution allows that the dose setting scale may contain at least 50, 60, 70, 80, 90, 100 units with an incremental of one.

Figure 1:
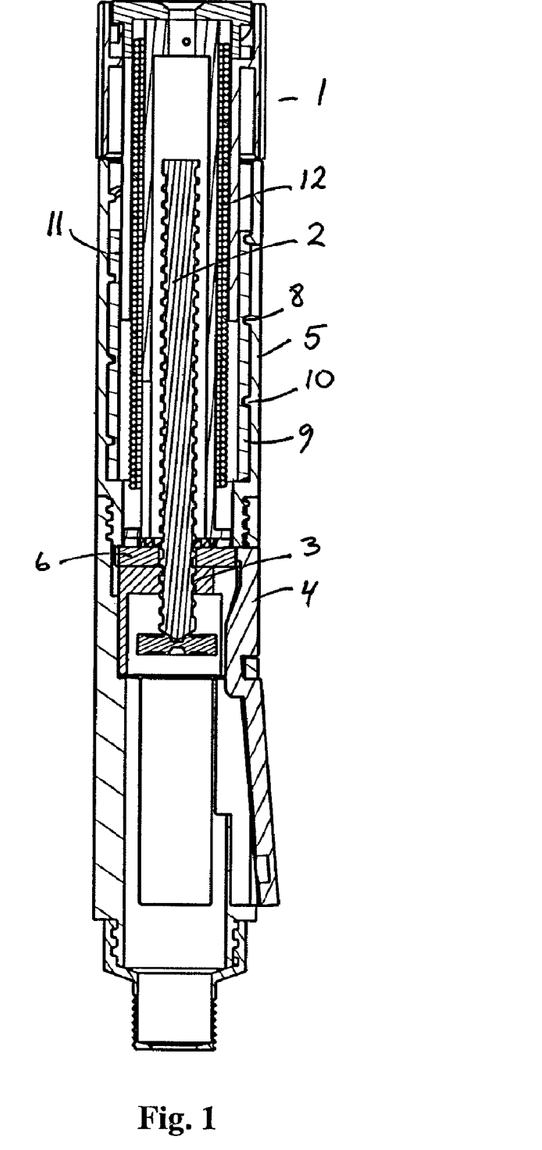
FIG. 1 shows a cross-sectional view of a first embodiment of the injection device according to the present invention.
Figure 2:
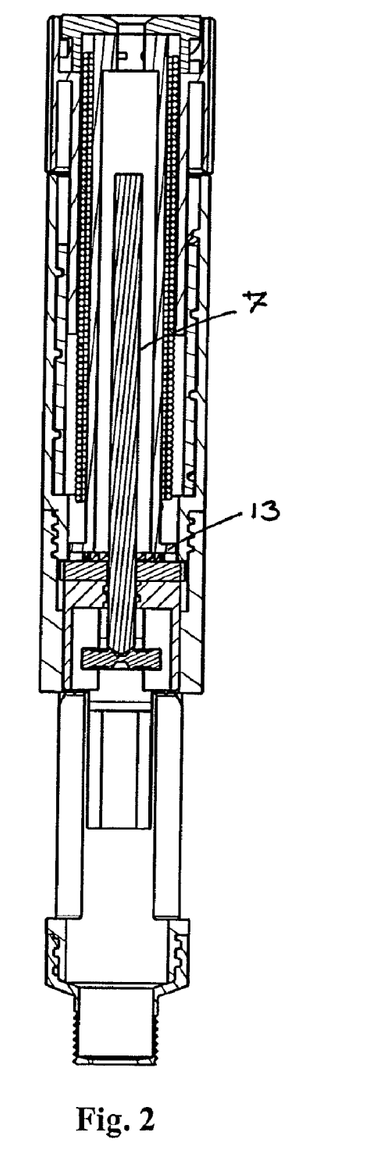
FIG. 2 shows a cross-sectional view (rotated 90 degrees compared to FIG. 1) of a first embodiment of the injection device according to the present invention.
Figure 3:
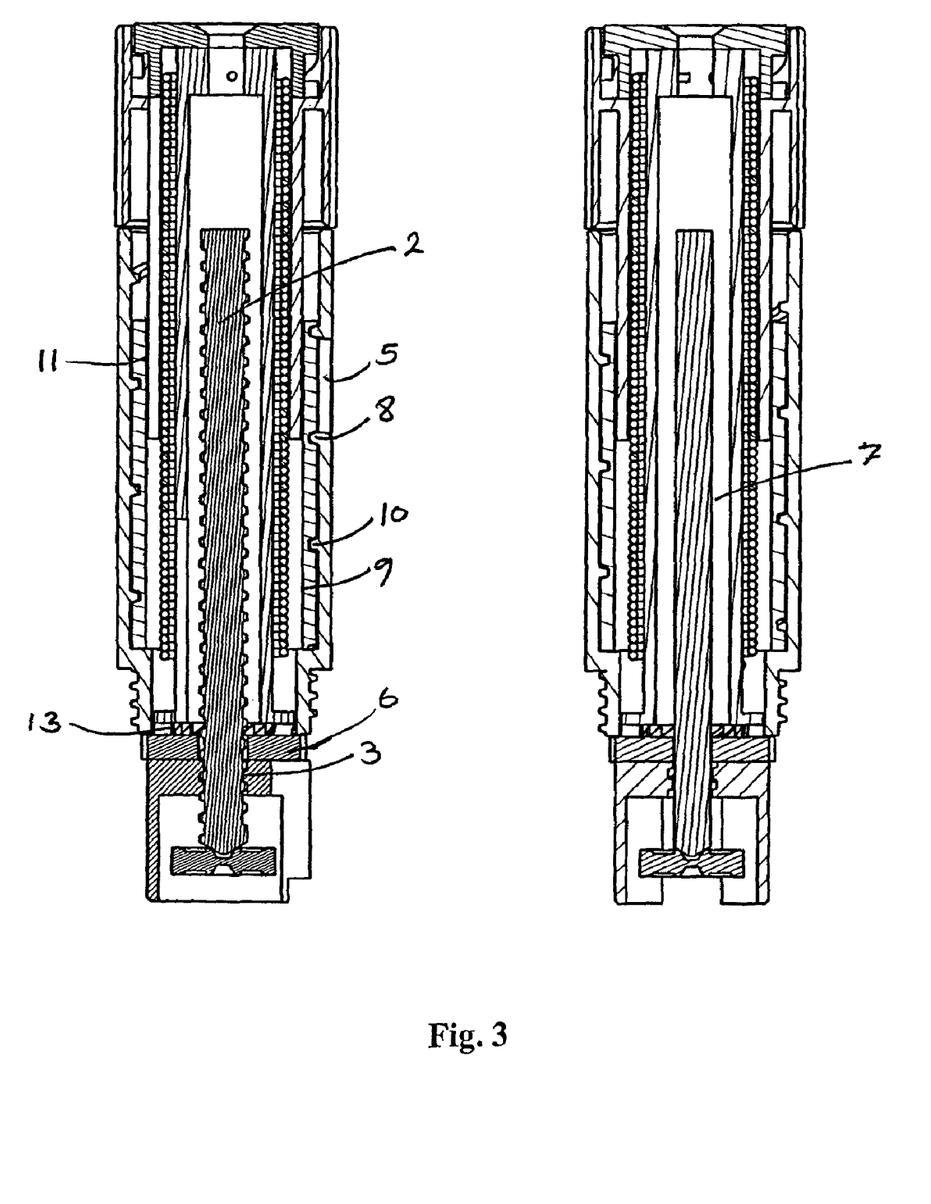
FIG. 3 shows a detailed cross-sectional view of a first embodiment of the present invention.

FIGS. 1-3 show a cross-sectional view of the injection device according to a first embodiment of the present invention. The dose of medicament to be ejected from the injection device is set by rotating dose setting member 1. The dose setting member 1 is attached to the housing 5 of the injection device via torsion spring 12. When the dose setting member 1 is rotated in order to set a dose to be ejected from the injection device, energy is accumulated in torsion spring 12. This energy may be released by releasing locking member 4 whereby the piston rod 2 will rotate and move in the distal direction of the injection device. The distal movement of the piston rod 2 is caused by a rotational movement of the piston rod 2 itself in that the piston rod 2 has a threaded outer surface. The threads of the piston rod 2 engage and co-operate with a threaded portion 3 of the injection device causing the piston rod 2 to perform the distal and axial movement.

The inner surface of housing 5 of the injection device is provided with threads 10. These threads are adapted to engage and co-operate with outer threads 8 of a dose indicator barrel 9. The dose indicator barrel 9 engages with sliding track 11 of the dose setting member 1 in such a way that the dose indicator barrel 9 is able to slide in said sliding track 11 in an axial direction of the injection device.

When the dose setting member 1 is rotated in order to set a dose, the dose indicator barrel 9 rotates with the dose setting member 1 causing the dose indicator barrel 9 to be axially displaced relative to the housing 5. A window is provided in the housing 5 of the injection device. Through this window, the user of the injection device may view the actual dose setting level from numerals (not shown) provided on an exterior surface of the dose indicator barrel 9. The numerals are arranged along a helical path.

An advantage of having the numerals arranged along a helical-like path is that a higher angular resolution is obtainable when a dose is to be set. Due to this higher angular resolution a dose can be set with a significantly higher accuracy. This greater accuracy is obtained since the helical-like path allows for more numerals to be arranged on the dose indicator barrel 9 compared to numerals arranged at the same height on the surface of the dose indicator barrel 9.

When a dose has been ejected from the injection device, the dose indicator barrel 9 is adapted to be rotated back to its initial position and it is thereby ready to be set to a new dose. The same applies for an injection device applying a counting device as a dose meter.

As already mentioned, the piston rod 2 has a threaded outer surface. This threaded outer surface engages and co-operates with a threaded portion 3 of the injection device. The piston rod 2 is driven by the drive member 6 that engages a track in piston rod 2. The axial movement of the piston rod 2 is provided by rotating piston rod 2 in the threaded portion 3 of the injection device. Drive member 6 may be locked by the locking member 4. In its locked position, drive member 6 is prevented from rotating. In order to release the drive member 6, the user of the injection device may activate a push button 15 whereby drive member 6 causes the piston rod 2 to rotate in threaded part 3 of the housing whereby the piston rod 2 rotates and travels in the distal direction of the injection device. Thus, when the drive member 6 is released, the injection device ejects automatically. During ejection, the dose indicator barrel returns to zero dose. The push button may be spring loaded.

The dose setting member 1 and the drive member 6 are mechanically connected via a self-tightening ratchet 13. Preferably, the self-tightening ratchet 13 has saw-toothed teeth with approximately vertical oriented flanks as the self-tightening flanks.

In order to reset or reduce an already set dose, the dose setting member 1 is arranged to be axially retractable over a distance corresponding to the height of the teeth of the one-way ratchet 13. Thus, by pulling the dose setting member 1 back, and thereby disengage the dose setting member 1 from the drive member 6, an already set dose can be reduced or even reset. The amount of reduction obviously depends on the angle of rotation (in the opposite rotation direction as when a dose is set) of the dose setting member 1.

The self-tightening ratchet may be formed as a separate component having first and second engaging parts. Alternatively, one of these parts may form an integral part of the dose setting member 1, or alternatively, an integral part the drive member 6.

Figure 4:
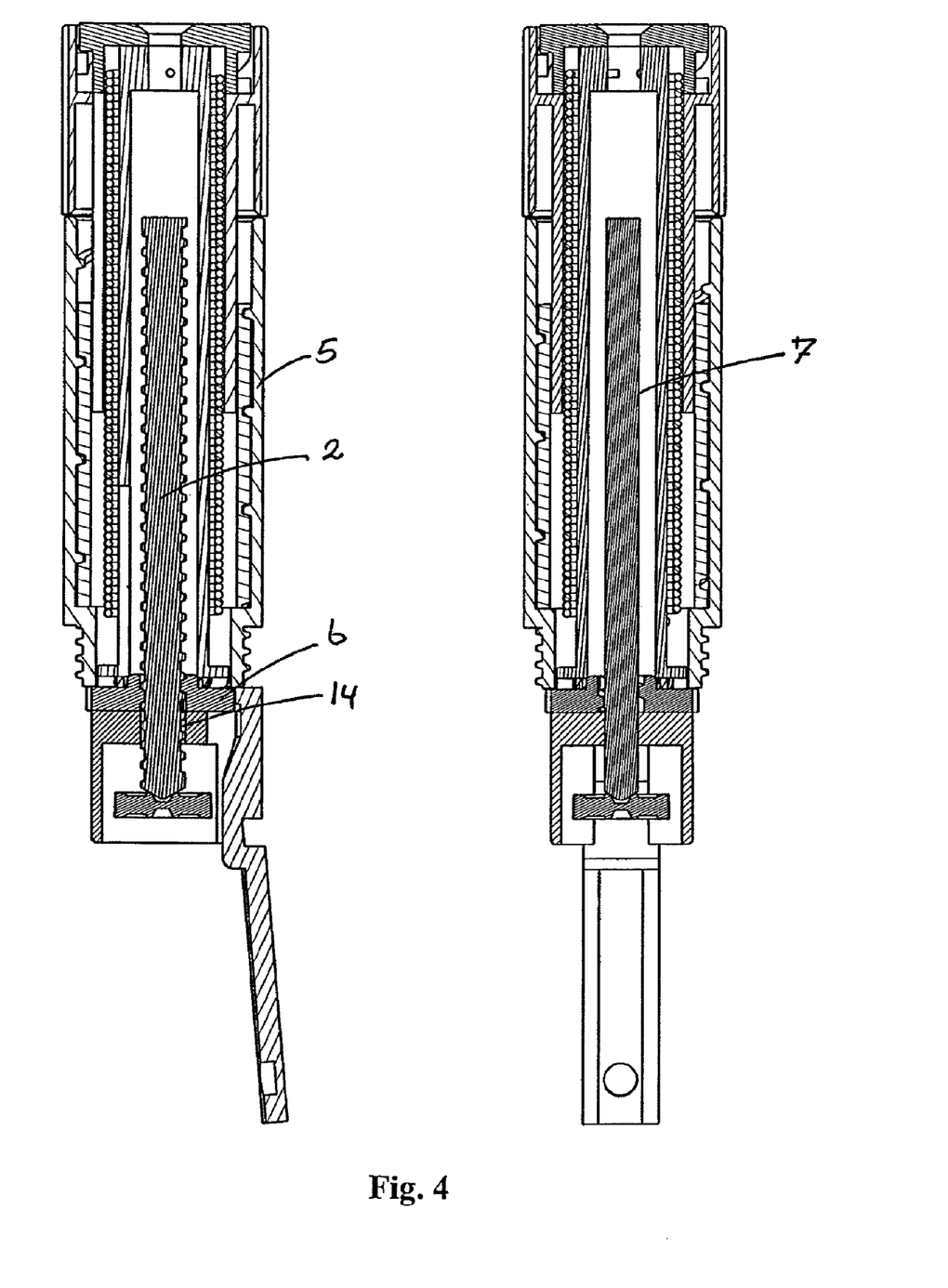
FIG. 4 shows a detailed cross-sectional view of a second embodiment of the present invention.
Figure 7:
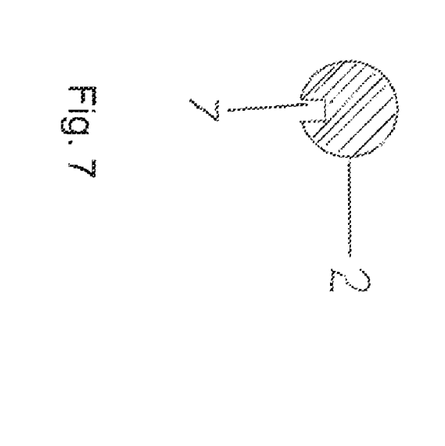
FIG. 7 shows a cross-sectional view of a track in a piston rod.

FIG. 4 shows a second embodiment of the present invention. Compared to the first embodiment, the drive member 6 has a threaded portion cooperating with the threaded outer surface of the piston rod 2. The main difference compared to the first embodiment is that the piston rod 2 is no longer rotatable relative to the housing 5. This non-rotatable relationship is ensured in that the housing of the injection device has a key 14 which at least partly engages the track 7 of piston rod 2. Thus, when the drive member 6 is free to rotate relative to the housing 5 the piston rod 2 will undergo a translational movement along the axial direction of the injection device.

Figure 5:
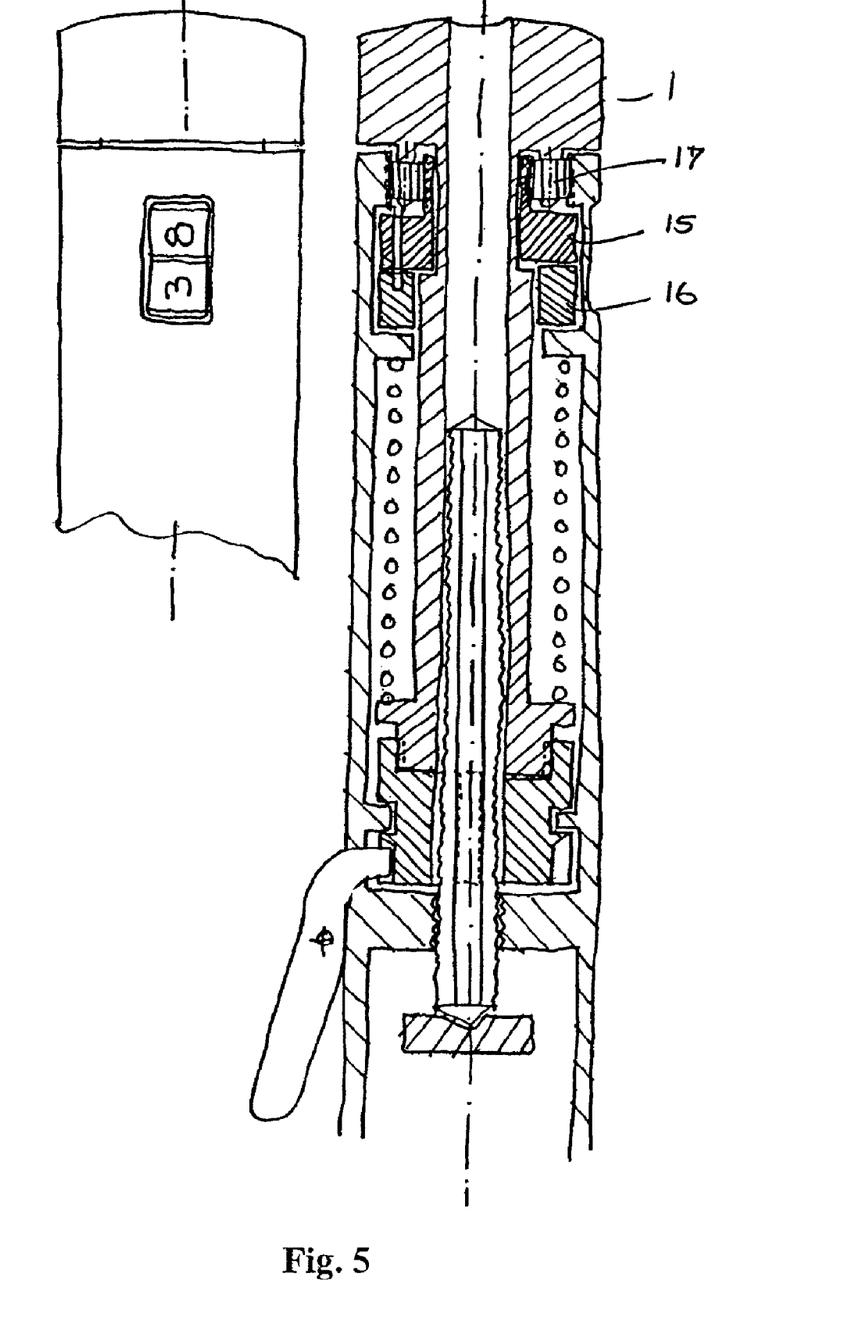
FIG. 5 shows a detailed cross-sectional view of a third embodiment of the present invention.
Figure 6:
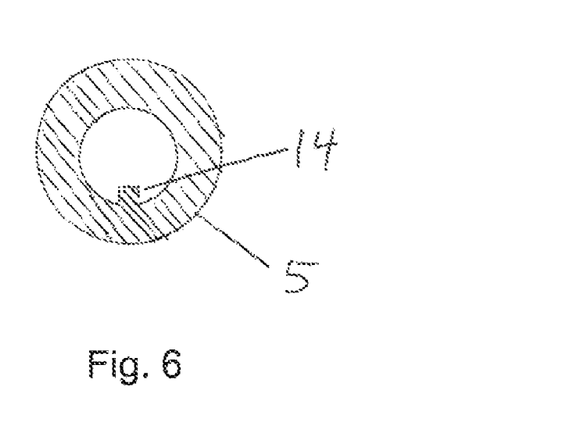
FIG. 6 shows a cross-sectional view of a key.

FIG. 5 shows a third embodiment of the present invention. In this embodiment the dose indicator barrel of the first and second embodiment has been replaced by a counting device having two wheels 15, 16. In principle the number of wheels may be chosen arbitrary, but for simplicity, a counting device having only two wheels is illustrated in FIG. 5. The counting device is operated as follows: When the dose setting member 1 is rotated, the wheel closest to the dose setting member 15 is rotated via an optional planet gear 17. This wheel contains numerals with an incremental of one. The total scale on this wheel may contain 10 units distributed over a scale from 0 to 9, or alternatively, the total scale may contain for example 20 units distributed over two scales each having a scale from 0 to 9.

The second wheel 16 next to the first wheel 15 also contains numerals with an incremental of 1. However, this second wheel "counts" the number of revolutions of the first wheel, or alternatively, it "counts" the tens of the first wheel with an incremental of one. Alternatively, the second wheel "counts" the number of half resolutions of the first wheel in case the first wheel contains a scale having 20 units.

The invention claimed is:

1. An injection device comprising
a helical torsion spring (12) operatively connected to a dose setting member (1), the dose setting member (1) being adapted to set a dose to be ejected from the injection device, and
a rotatably mounted display member adapted to display the dose to be ejected from the injection device in accordance with a setting of the dose setting member (1), the rotatably mounted display member being rotatable over an angle corresponding to at least one revolution of the display member, and wherein the device further comprises a drive member for driving a non-rotating threaded piston rod, the drive member having a threaded surface for engaging the thread on the piston rod, the drive member being rotatable within the device but axially fixed and wherein a ratchet couples the dose setting member to the drive member so that the dose setting member is moveable in a first direction to set a dose, the first direction being against the bias of the torsion spring, and being moveable in a second direction with the bias of the spring in order to reset or reduce a set dose without rotating the drive member, and wherein the ratchet retains the dose setting member from rotating under influence of the spring and wherein upon release of a latch the spring drives the drive member to rotate, thereby axially advancing the piston rod, and wherein rotation of the drive member is accompanied by rotation of the dose display member which returns to a zero position upon completion of the ejection of the dose.

2. An injection device according to claim 1, wherein the display member is adapted to be moved between two end positions, said two end positions defining an operation range of the display member, said operation range being associated with a substantially linear working range of the torsion spring.

3. An injection device according to claim 1, wherein the display member comprises a dose indicator barrel (9) having numerals arranged along a helical path on an outer surface thereof and wherein the dose indicator barrel threadly engages a housing surface on the interior of the device so that rotational motion of the dose indicator barrel results in its axial translation.

4. An injection device according to claim 1, wherein the display member comprises a counting device having two or more display wheels having numerals arranged on an outer surface thereof.

5. An injection device according to claim 2, further comprising
   a housing (5),
   a piston rod (2) having a threaded outer surface with a drive track (7) arranged in a longitudinal direction of said outer surface,
wherein the dose setting member (1) is rotatably mounted and defines a passage for the piston rod (2), the dose setting member (1) further having a guiding track (11) arranged on an inner surface thereof,
   a rotatable drive member (6) being adapted to at least partly engage with at least part of the drive track (7) of the piston rod (2) so as to drive the piston rod,
wherein the dose indicator barrel (9) has a part engaging at least part of the guiding track (11) of the dose setting member (1), the dose setting member (1) and the dose indicator barrel (9) being movable in relation to each other, the dose indicator barrel (9) further having a threaded outer surface (8) cooperating with a threaded inner portion (10) of the housing (5) whereby the dose indicator barrel (9) undergoes a combined translational and rotational movement in relation to the housing (5) upon rotation of the dose setting member (1), and wherein the injection device has a threaded portion (3) cooperating with the threaded outer surface of the piston rod (2) so that rotation of the piston rod (2) relative to the housing (5) results in a longitudinal movement of the piston rod (2).

6. An injection device according to claim 2, further comprising
   a housing (5),
   a piston rod (2) having a threaded outer surface with a track (7) arranged in a longitudinal direction of said outer surface,
wherein the dose setting member (1) is rotatably mounted and defines a passage for the piston rod (2), the dose setting member (1) further having a guiding track (11) arranged on an inner surface thereof,
   a rotatable drive member (6) having a threaded portion cooperating with at least part of the threaded outer surface of the piston rod (2),
wherein the dose indicator barrel (9) has a part engaging at least part of the guiding track (11) of the dose setting member (1), the dose setting member (1) and the dose indicator barrel (9) being movable in relation to each other, the dose indicator barrel (9) further having a threaded outer surface (8) cooperating with a threaded inner portion (10) of the housing (5) whereby the dose indicator barrel (9) undergoes a combined translational and rotational movement in relation to the housing (5) upon rotation of the dose setting member (1), and wherein the injection device has a portion at least partly engaging the track (7) of piston rod (2) so that rotation of the drive member (6) relative to the housing (5) results in a longitudinal movement of the piston rod (2).

7. An injection device according to claim 5, wherein the drive member (6) is adapted to be connected to the dose setting member (1) via a ratchet (13).

8. An injection device according to claim 5, wherein the torsion spring (12) is arranged between the housing (5) and the dose setting member (1) in such a way that when the dose setting member (1) is rotated around the piston rod (2), the torsion spring (12) is strained.

9. An injection device according to claim 5, further comprising a stopping member for defining an outer position of the dose indicator barrel (9), the outer position of the dose indicator barrel (9) corresponding to a maximum obtainable dose.

10. The injection device of claim 9, wherein axial movement of the display member does not cause the spring to work outside a substantially linear working range.

11. An injection device according to claim 1, further comprising a release button adapted to release the locking member (4) from its locking position and wherein the display undergoes a rotational and translation movement during operation of the device.

12. An injection device according to claim 11, wherein the release button is positioned in the distal half of the length of the injection device.

13. The apparatus of claim 1, wherein the piston rod is keyed to a component that is irrotatable with respect to the housing.

14. The injection device of claim 1, wherein axial movement of the display member does not cause the spring to operate outside a substantially linear working range.

15. The injection device of claim 1, wherein axial movement of the display member does not cause the spring to work outside a substantially linear working range.

16. A dose setting and injecting apparatus for assisting in the setting and ejection of a dose of medication from an injection device; the apparatus comprising
   a. a housing component;
   b. a dose setting member capable of being rotated over an angle larger than 360 degrees;
   c. a dose indicator barrel having a helical display of numerals arranged thereon and that rotates back to an initial position during ejection of a dose of medication and that moves axially during rotation;
   d. a piston rod (2) having a threaded surface, the piston rod being non-rotatable relative to the housing;
   e. a drive member (6) having an internal thread that engages a portion of the threaded surface on the piston rod, the drive member being rotatable relative to the housing so that when it rotates it causes axial translation of the piston rod;
   f. a releasable locking member (4) that rotatably locks in a releasable manner the driver member so that it does not rotate relative to the housing component;

g. a helical torsional spring which extends coaxially with the piston rod and which interconnects with the dose setting member in such a way that rotation of the dose setting member in a direction that sets a dose strains the spring;

h. a ratchet coupling the dose setting member to the drive member, the ratchet allowing a dose to be set by a procedure that consists of dialing up a dose against the strain of the spring to set a dose size and, when necessary, dialing the dose setting member in an opposite direction to reduce the size of the dose, wherein the ratchet allows the dose setting member to be dialed in an up and a down direction without rotation of the drive member but where the ratchet prevents the torsional spring from rotating the dose setting member in a downward, dose reducing direction;

wherein when the releasable locking member is released, the drive member is free to rotate under the influence of the spring and thereby drives the piston rod in an axial direction to expel a drug from the device.

17. The apparatus of claim 16, wherein the spring is coupled directly between the housing and the dose setting member.

18. The apparatus of claim 16, wherein the spring is operably coupled to the dose setting member at one portion and operably fixed with respect to the housing another portion, so that rotation of the dose setting member relative to the housing strains the spring.

19. The apparatus of claim 18, wherein the latch member moves axially to release the drive member.

20. The apparatus of claim 18, wherein the piston rod is keyed to prevent rotation.

21. The apparatus of claim 16, wherein the dose indicator barrel moves axially in a first direction during setting of a dose and axially in an opposite direction during injection of the dose.

22. The apparatus of claim 16, 17, 18, or 21, wherein the dose indicator rotates back to an initial position as an ejection is being completed.

23. The apparatus of claim 22, wherein the dose indicator barrel is integral with the dose setting member.

24. The apparatus of claim 16, wherein the dose indicator barrel or the dose setting member is threadedly engaged with an element fixed to the housing portion.

25. The apparatus of claim 16, wherein the latch member moves axially to release the drive member.

26. The apparatus of claim 16, or 20, wherein the dose setting member may be separated from the drive member by relative axial movement between the two.

27. The injection device of claim 26, wherein axial movement of the display member does not cause the spring to work outside as substantially linear working range.

28. A dose setting and injecting mechanism for an injection device, the mechanism comprising:
a rotatable dose setting member being rotatable over more than one revolution;
a dose indicator barrel that has a helical scale of numerals disposed thereon, the dose indicator barrel translating axially when rotated;
a threaded non-rotating piston rod, the piston rod being driveable in a distal direction to expel a dose of medication;
a rotatable but axially fixed drive member containing a thread that engages the thread on the piston rod;
a torsional spring for storing energy needed to expel a dose of medication, the torsional spring being helical, the torsional spring being operable connected to the dose setting member so that when a dose is dialed up energy for ejecting medication is stored in the spring;
a ratchet mechanism coupling the dose setting member with the drive member and allowing the dose setting member to be rotated over more than one revolution in a dose setting direction and to be rotated in a dose reducing direction without rotating the drive member, wherein the ratchet mechanism provides sufficient force to prevent the dose setting member from counter rotating under the influence of a force from the torsional spring;
a releasable lock that prevents rotation of the drive member until it is released, thereby allowing the torsional spring to remain strained until it is released when performing an ejection; and
wherein upon release of the lock, energy from the spring drives the drive member to rotate which drives the piston rod in a distal direction and simultaneously the dose indicator barrel is rotated to an initial position so that upon completion of the expulsion of the dose another dose can immediately be set and ejected.

29. An injection device comprising:
a rotatable dose setting member being rotatable over more than one revolution;
a dose indicator barrel that has a helical scale of numerals disposed thereon, the dose indicator barrel translating axially when rotated;
a threaded non-rotating piston rod, the piston rod being driveable in a distal direction to expel a dose of medication;
a rotatable but axially fixed drive member containing a thread that engages the thread on the piston rod;
a torsional spring for storing energy needed to expel a dose of medication, the torsional spring being helical, the torsional spring being operable connected to the dose setting member so that when a dose is dialed up energy for ejecting medication is stored in the spring;
a coupling mechanism connecting the dose setting member with the drive member and allowing the dose setting member to be rotated over more than one revolution in a dose setting direction and to be rotated in a dose reducing direction without rotation of the drive member, wherein the coupling mechanism provides sufficient force to prevent the dose setting member from counter rotating under the influence of a force from the torsional spring;
a releasable lock that prevents rotation of the drive member until it is released; and
wherein upon release of the lock, energy from the spring drives the drive member to rotate which drives the piston rod in a distal direction and simultaneously the dose indicator barrel is rotated toward an initial position so that upon completion of the expulsion of the dose another dose can immediately be set and injected; and
wherein the torsional spring operates over a substantially linear working range.

30. The injection device of claim 29, wherein the torsional spring is operably coupled at one end to a housing and is operably coupled to the dose setting member at another end and wherein the coupling mechanism allows the spring to be wound during dose setting and retains the spring in a strained position, and wherein the coupling mechanism allows the spring to be unwound during ejection of a dose by allowing it to rotate the drive member and wherein prior to ejection the coupling mechanism allows the resetting or reduction of a dose by allowing the dose setting member to be dialed down.

* * * * *

UNITED STATES PATENT AND TRADEMARK OFFICE
CERTIFICATE OF CORRECTION

| | | |
|---|---|---|
| PATENT NO. | : 8,357,120 B2 | Page 1 of 1 |
| APPLICATION NO. | : 11/665571 | |
| DATED | : January 22, 2013 | |
| INVENTOR(S) | : Claus Schmidt Moller | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 495 days.

Signed and Sealed this
Eleventh Day of November, 2014

Michelle K. Lee
*Deputy Director of the United States Patent and Trademark Office*